(12) United States Patent
Holtzapple et al.

(10) Patent No.: US 7,820,417 B2
(45) Date of Patent: Oct. 26, 2010

(54) METHODS AND SYSTEMS FOR BIOMASS CONVERSION TO CARBOXYLIC ACIDS AND ALCOHOLS

(75) Inventors: Mark Thomas Holtzapple, College Station, TX (US); Richard Davison, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 486 days.

(21) Appl. No.: 11/153,978

(22) Filed: Jun. 16, 2005

(65) Prior Publication Data

US 2006/0024801 A1 Feb. 2, 2006

Related U.S. Application Data

(60) Provisional application No. 60/580,291, filed on Jun. 16, 2004.

(51) Int. Cl.
*C12P 7/40* (2006.01)
*C12P 7/64* (2006.01)

(52) U.S. Cl. ........................ 435/136; 435/134

(58) Field of Classification Search ........................ None
See application file for complete search history.

(56) References Cited

U.S. PATENT DOCUMENTS

| | | | | |
|---|---|---|---|---|
| 5,892,109 | A * | 4/1999 | Baniel et al. | 562/580 |
| 5,962,307 | A | 10/1999 | Holtzapple et al. | 435/294.1 |
| 5,986,133 | A | 11/1999 | Holtzapple et al. | 562/608 |
| 6,041,392 | A | 3/2000 | Kanamaru et al. | 711/113 |
| 6,395,926 | B1 | 5/2002 | Holtzapple et al. | 562/513 |
| 6,472,559 | B2 * | 10/2002 | Baniel et al. | 562/580 |
| 6,478,965 | B1 | 11/2002 | Holtzapple et al. | 210/634 |
| 7,601,865 | B2 * | 10/2009 | Verser et al. | 562/508 |
| 2006/0024801 | A1 * | 2/2006 | Holtzapple et al. | 435/136 |
| 2008/0176301 | A1 * | 7/2008 | Granda et al. | 435/157 |

FOREIGN PATENT DOCUMENTS

| | | |
|---|---|---|
| WO | 9410112 A | 5/1994 |
| WO | 2004041995 A | 5/2004 |

OTHER PUBLICATIONS

International PCT Search Report with Written Opinion, PCT/US2005/021337, 12 pages, mailed Jul. 11, 2006.
The First Office Action (PCT Application in the National Phase) from The Patent Office of the State Intellectual Property Office of the People's Republic of China, Application No. 2005-80019714.6, dispatch dated Aug. 14, 2009 and received Sep. 7, 2009, includes English translation of the Text of the First Office Action, 6 pages.

\* cited by examiner

*Primary Examiner*—Herbert J. Lilling
(74) *Attorney, Agent, or Firm*—Conley Rose, P.C.

(57) ABSTRACT

The disclosure includes a method, process and apparatus for the conversion of biomass to carboxylic acids and/or primary alcohols. The system may include a pretreatment/fermentation subsystem operable to produce a fermentation broth containing carboxylic acid salts from biomass, such as lignocellulosic biomass. The system may also include a dewatering subsystem operable to remove excess water from the fermentation broth to produce a concentrated product. The system may also includes an acid springing subsystem operable to produce a mixed carboxylic acid product. The system may also include a hydrogenation subsystem operable to produce an alcohol mixture, such as a mixture containing primary alcohols. Methods of operating this system or other systems to obtain a carboxylic acid or alcohol mixture are also provided.

14 Claims, 5 Drawing Sheets

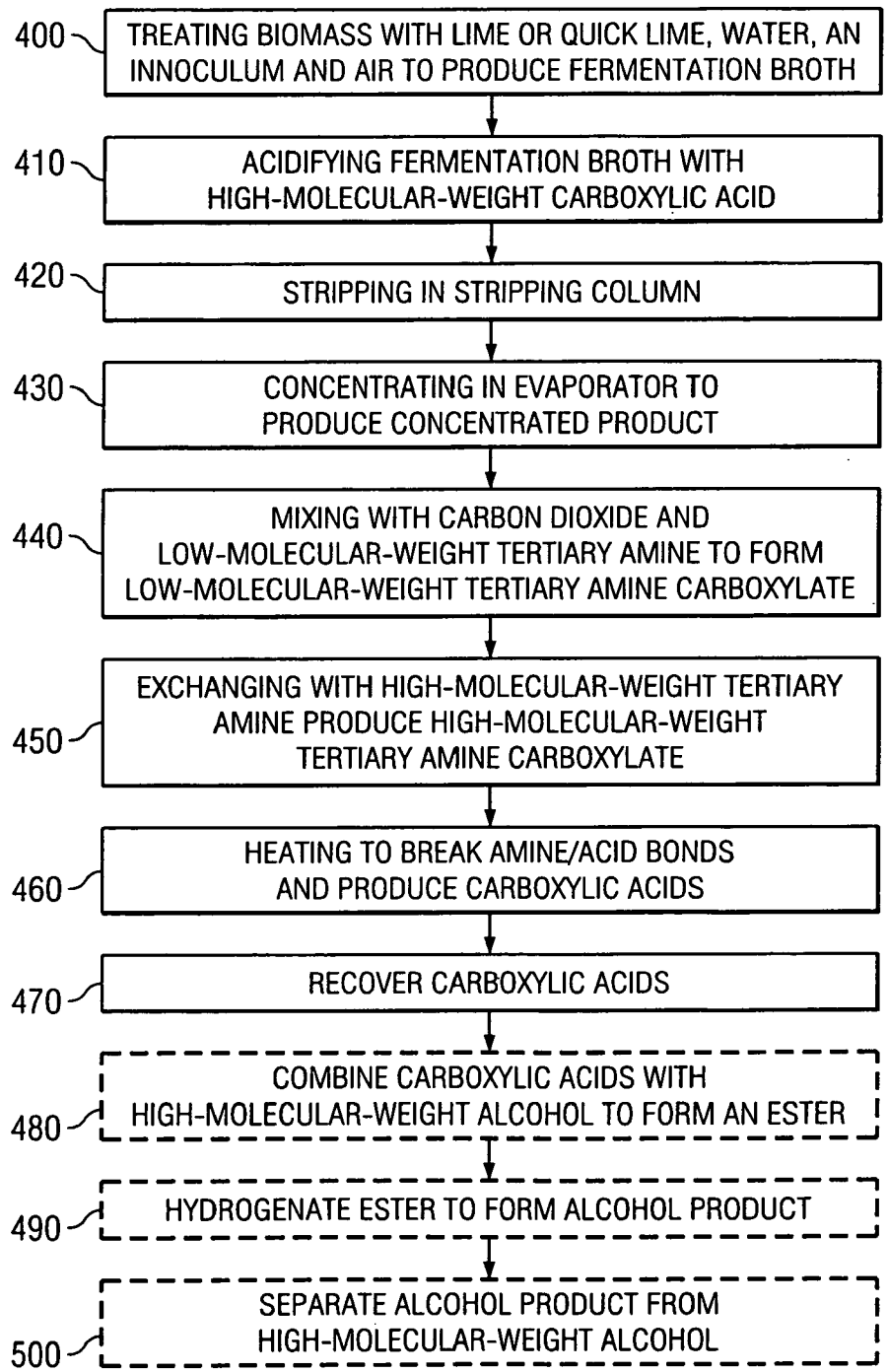

METHODS AND SYSTEMS FOR BIOMASS CONVERSION TO CARBOXYLIC ACIDS AND ALCOHOLS

CROSS-REFERENCE TO RELATED APPLICATION

This application claims priority to U.S. Provisional Application No. 60/580,291 filed Jun. 16, 2004.

TECHNICAL FIELD

The present invention relates to methods of converting biomass to useful substances, such as carboxylic acids and primary alcohols, through an integrated pretreatment, fermentation, dewatering and treatment process. More specifically it may relate to a method applied to lignocellulosic biomass.

BACKGROUND

A great deal of biomass, particularly lignocellulosic biomass, remains unused or inefficiently used during agricultural and industrial processes. Disposal of this biomass is often difficult or costly. Therefore, methods of using this biomass to produce useful chemicals are quite valuable.

Organic acids are important chemicals of commerce. Historically, organic acids were produced from animal fat or vegetable oil sources or from petroleum sources in substantially nonaqueous systems. More recently, organic acids have been identified as among the most attractive products for manufacture from biomass by fermentation. Alcohols are also important industrial chemicals that may be produced by fermentation of biomass. However, extraction of organic acids and alcohols from the overall fermentation product is not easy and is often inefficient in the use of energy, water and reactant chemicals.

SUMMARY OF THE INVENTION

The present invention includes a method, process and apparatus for the conversion of biomass to carboxylic acids and/or primary alcohols.

According to one embodiment, the invention includes a system for the conversion of biomass. The system includes a pretreatment/fermentation subsystem operable to pretreat biomass with lime or quick lime and air to produce treated biomass and ferment the treated biomass with an inoculum to produce a fermentation broth containing carboxylic acid salts. The system also includes a dewatering subsystem operable to remove excess water from the fermentation broth to produce a concentrated product. Finally, the system includes an acid springing subsystem operable to combine the concentrated product with a low-molecular-weight tertiary amine or ammonia to produce a low-molecular-weight tertiary amine or ammonia carboxylate product from the carboxylic acid salts, replace the low-molecular-weight tertiary amine or ammonia in the low-molecular-weight tertiary amine or ammonia carboxylate product with a high-molecular-weight tertiary amine to form a high-molecular-weight tertiary amine carboxylate product, and thermally break the amine-carboxylate bonds in the high-molecular-weight tertiary amine carboxylate product to produce a mixed carboxylic acid product.

In a more specific embodiment the system may also include a hydrogenation subsystem operable to combine the mixed carboxylic acid produce with a high-molecular-weight alcohol to form an ester, convert the ester to an alcohol mixture using a hydrogenation catalyst, and separate the alcohol mixture from the high-molecular-weight alcohol.

According to another embodiment, the invention includes a method of obtaining a fermentation product. The method may include: treating a pile of biomass with lime or quick lime, water, an inoculum and air to produce a fermentation broth; acidifying the fermentation broth with a high-molecular-weight carboxyllic acid to produce acidified fermentation broth; stripping the fermentation broth in a stripping column to produce stripped fermentation broth; concentrating the stripped fermentation broth in an evaporator to produce concentrated product; mixing the concentrated product with a low-molecular-weight tertiary amine or ammonia and carbon dioxide to produce a low-molecular-weight tertiary amine or ammonia carboxylate; exchanging the low-molecular-weight tertiary amine or ammonia carboxylate with a high-molecular-weight tertiary amine to produce a high-molecular-weight tertiary amine carboxylate; heating the high-molecular-weight tertiary amine carboxylate to a temperature sufficient to break acid/amine bonds to produce a free carboxylic acid product; and recovering the free carboxylic acid product.

In a more specific embodiment, the method may also include: combining the carboxylic acid produce with a high-molecular-weight alcohol to from an ester; hydrogenating the ester to form an alcohol product; separating the high-molecular-weight alcohol from the alcohol product; and recovering the alcohol product.

BRIEF DESCRIPTION OF THE DRAWINGS

The present invention may be better understood through reference to the following detailed description, taken in conjunction with the drawings, in which:

FIG. 5 illustrates a biomass converting system, according to an embodiment of the present invention; and FIG. 6 illustrates a flow diagram of a method for producing carboxylic acids and alcohols, according to an embodiment of the invention.

DETAILED DESCRIPTION

The present invention relates to systems, methods, and devices for the conversion of biomass, particularly lignocellulosic biomass, to carboxylic acids and alcohols, particularly primary alcohols.

Figure 1:
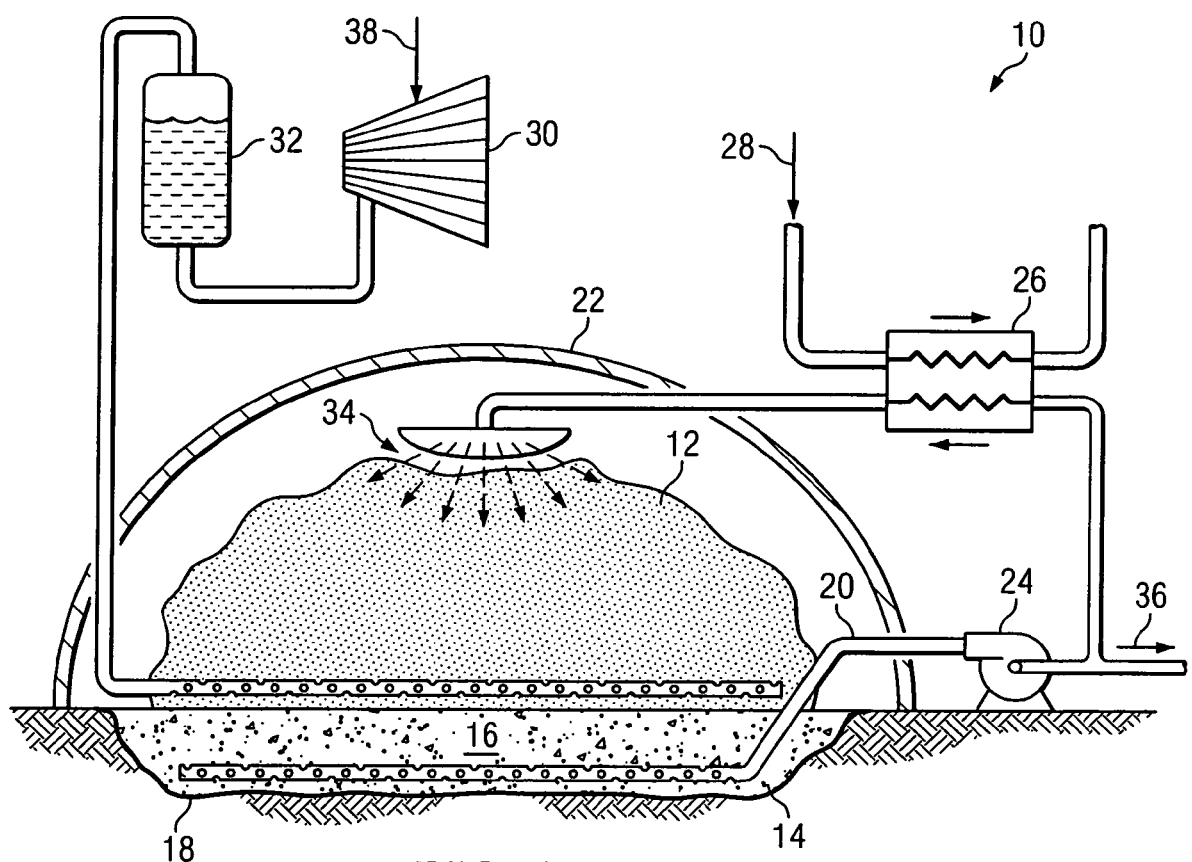
FIG. 1 illustrates a pretreatment and fermentation system, according to an embodiment of the present invention.

Referring now to FIG. 1, pretreatment and filtration system 10 may be provided in which biomass pile 12 may be blended with lime or quick lime (calcium carbonate or calcium oxide) and carbon dioxide (not shown) and piled on top of pit 14 filled with gravel 16. Pit 14 may also be lined with liner 18. Biomass pile 12 may include any sort of biomass. In selected embodiments it may include lignocellulosic biomass, such as processed sugarcane or sorghum stalks or corn stover. Perforated drain pipe 20 may be embedded in gravel 16. Biomass pile 12 may be covered by cover 22 to keep out rain and debris, particularly if system 10 is outside. Pump 24 may circulate water 34 from pit 14 to the top of biomass pile 12. As water 34 circulates through pile 12, it may flow through heat exchanger 26, which may regulate the temperature. Cooling water or heat source 28 may also circulate through heat exchanger 26.

During approximately the first month after biomass pile 12 is assembled, air 38 may be blown through pile 12 using blower 30. To remove carbon dioxide from the air, it may be bubbled through lime water slurry 32. Oxygen-rich air 28 may also be supplied. The combined effect of lime plus air 28 in pile 12 removes lignin from the biomass, rendering it more digestible. Further, the lime removes acetyl groups from hemicellulose, which also helps digestibility. Once the lime is exhausted, the pH drops to near neutral, at which point a mixed-culture inoculum may be added.

The inoculum may be derived from any source, but in many embodiments it may be derived from soil. Organisms derived from organic-rich soil in marine environments appear to be particularly well-suited for use with embodiments of the present invention. Such organisms are able to be productive in high-salt environments. For example, the inoculum may include a salt-tolerant microorganism.

After inoculation, the organisms digest the biomass and convert it to carboxylic acids. These acids react with the calcium carbonate or calcium oxioide in pile 12, producing calcium carboxylate salts or other calcium salts that are dissolved in the water that circulates through the pile. This aqueous solution, called fermentation broth 36 may be harvested and sent for further processing.

Figure 2:
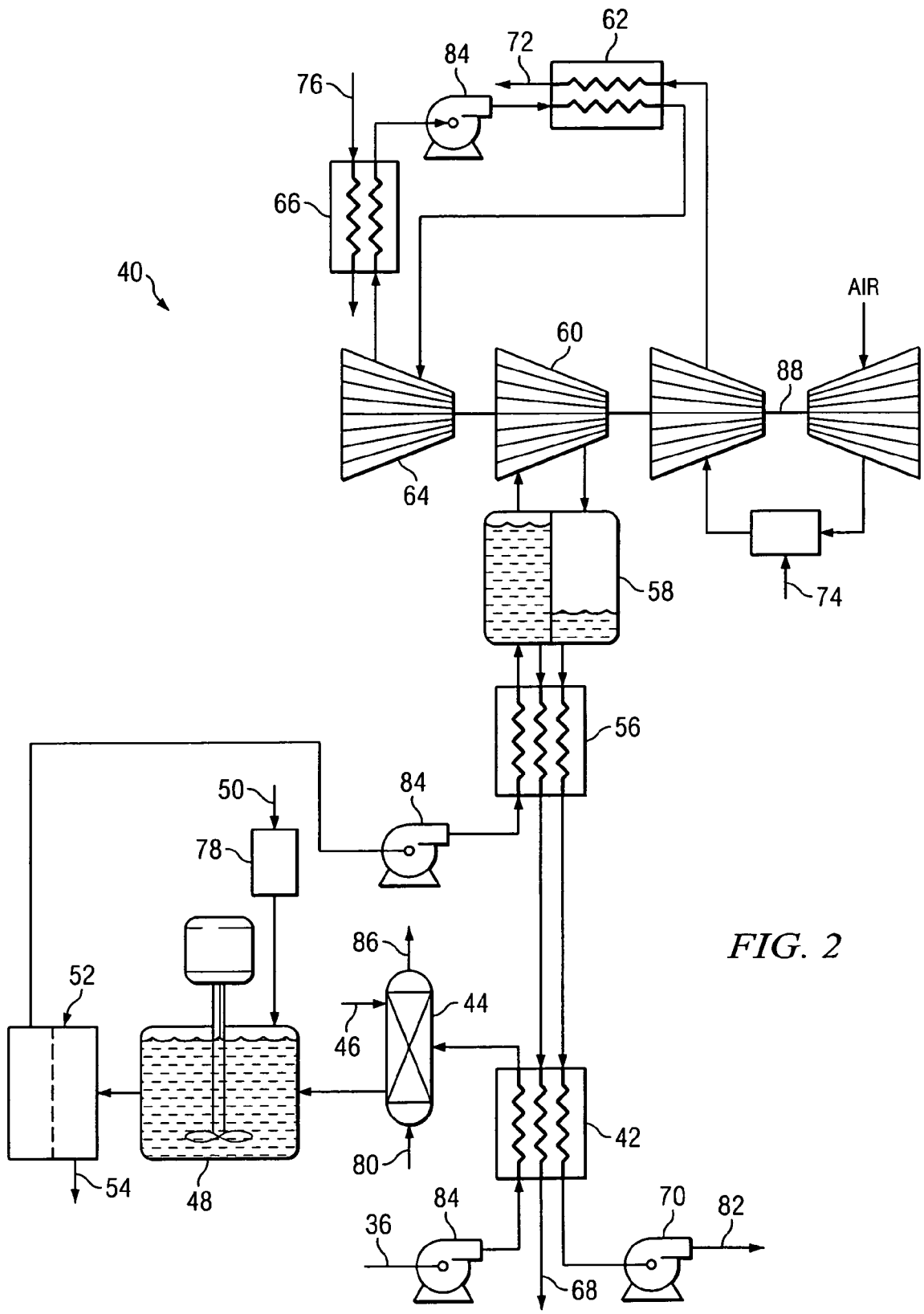
FIG. 2 illustrates a dewatering system, according to an embodiment of the present invention.

Referring now to FIG. 2, fermentation broth 36 may be dewatered in dewatering system 40. Fermentation broth 26 may be pumped through heat exchanger 42, which preheats the broth. Preheated fermentation broth 36 may then be acidified with high-molecular-weight carboxylic acid 46 (e.g. caproic, valeric, hepotanoic acids). Acidified fermentation broth 36 may be sent to stripping column 44 where steam 80 strips out dissolved carbon dioxide, a noncondensible gas that may interferes with evaporator 58 and cause calcium carbonate scaling on heat exchanger 56. Preferably, stripper 44 may operate at 1 atm, or higher, which allows exiting steam 86 to be used for heat elsewhere in the process. Further, if heat exchanger 42 becomes fouled by dissolved calcium carbonate, the pressure in stripper 44 may be reduced, which lowers the temperature of steam exiting heat exchanger 42 and may reduce fouling. However, if stripper 44 is operated at a reduced pressure, a vacuum pump (not shown) may be needed to remove the noncondensible gases from fermentation broth 36.

Steam-stripped, acidified fermentation broth 36 may then be sent to mixer 48 where the pH may be raised to between approximately 11 and 12 through the addition of lime 50 from reservoir 78, which causes scum 54 to precipitate. Scum 54 may then be removed in solids separator 52. This degassed, descummed fermentation broth 36 may be further heated in heat exchanger 56, after which it may enter evaporator 58. Compressor 60 may evaporate water from the low-pressure chamber of evaporator 58. The heat of condensation released in the high-pressure chamber of evaporator 58 may provide the heat of evaporation needed in the low-pressure chamber. The energy needed to drive the evaporation process may be provided by an engine.

In the embodiment shown in FIG. 2, a combined cycle engine may be used, which increases energy efficiency. Gas turbine 88 may provide shaft power to compressor 60. Gas turbine may use fuel 74. Exhaust gas 72 from gas turbine 88 may be directed to boiler 62, which may produce high-pressure steam that may drives steam turbine 64. Heat exchanger 66 may condense the low-pressure steam exiting steam turbine 64. Cooling water 76 may be used to facilitate this cooling. Distilled water 82 from the high-pressure section of evaporator 58 may be cooled in heat exchangers 56 and 42, and may be returned to pretreatment/fermentation system 10.

Concentrated product 68 may be cooled in heat exchangers 56 and 42, and sent to acid springing system 90. Liquid turbine 70 may recapture some work from the high-pressure liquids that exit evaporator 58.

Pumps 84 may be included at various points in the system to facilitate fluid flow.

Figure 3:
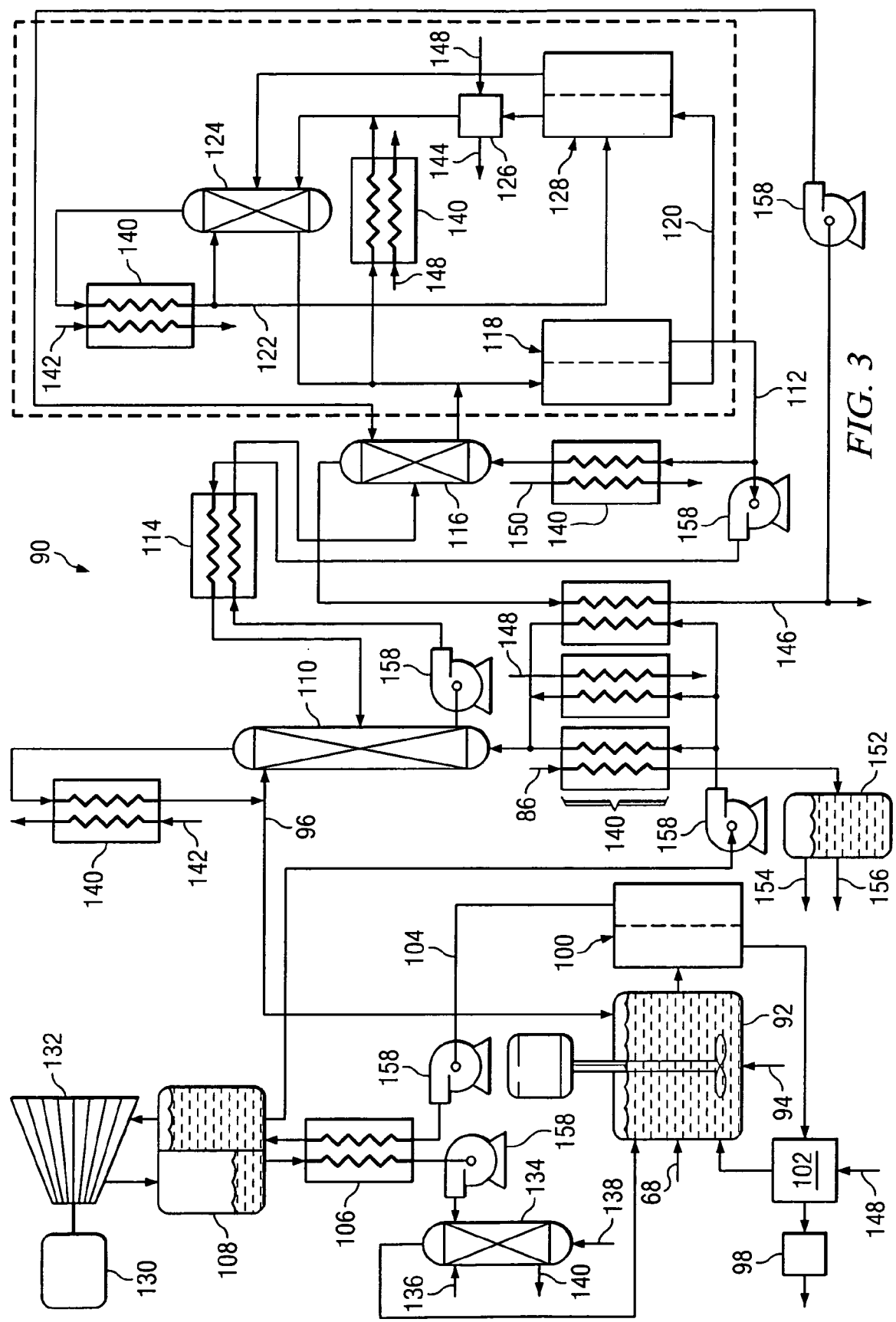
FIG. 3 illustrates an acid springing system, according to an embodiment of the present invention.

Referring now to FIG. 3, concentrated product 68 may next be sent to acid springing system 90. In mixer 92, concentrated product 68 from dewatering system 40 may be mixed with carbon dioxide 94 and low-molecular-weight tertiary amine 96, such as triethyl amine. The carboxylate reacts with low-molecular-weight tertiary amine 96 to form a soluble salt. The calcium reacts with carbon dioxide 94 to form insoluble calcium carbonate 98, which may be recovered using solids separator 100. Calcium carbonate 98 may then be washed with distilled water to remove adhering product and steam stripped in vessel 102 to ensure that all low-molecular-weight tertiary amine 96 is removed from calcium carbonate 98. Calcium carbonate 98 may then be sent to pretreatment/fermentation system 10 to act as a buffer or to a lime kiln (not shown) to be converted to lime.

Aqueous solution 104 contains dissolved low-molecular-weight tertiary amine carboxylate. It may then be preheated in heat exchanger 106 and sent to evaporator 108, where most of the water may be removed using the same vapor-compression technology used in dewatering system 40. Specifically, turbine 130 may provide energy to compressor 132. Waste fluid exiting evaporator 108 may be sent to column 134 where it may be combined with lime 136 and steam 138 to provide additional product stream to mixer 92 and water 140 to pretreatment/fermentation system 10.

The concentrated low-molecular-weight tertiary amine carboxylate solution 104 may then be sent to column 110 where high-molecular-weight tertiary amine 112, such as trioctyl amine or triethanol amine, may be added. Low-molecular-weight tertiary amine 96 may be replaced and exit the top of column 110, while high-molecular-weight tertiary amine carboxylate solution 104 may exit the bottom of column 110.

The high-molecular-weight tertiary amine carboxylate solution 104 may then be preheated in heat exchanger 114 and sent to column 116. In column 116, the temperature may be high enough to break chemical bonds, allowing the more volatile carboxylic acids 146 to exit the top of column 116. The less volatile high-molecular-weight tertiary amine 112 may exit the bottom of the column and may be recycled to column 110.

Any salts 120 that are in high-molecular-weight tertiary amine 112 may be removed using a solids separator 118. Recovered salts 120 may be washed with volatile solvent 122, such as triethyl amine, to remove high-molecular-weight tertiary amine 112 in separator 118. Solvent 122 may be separated from the recovered high-molecular-weight tertiary amine in distillation column 124. Salts 120 may then be steam stripped in stripper 126 to remove volatile solvent 122 and form solids 144.

System 90 may contain various heat exchangers 140 that may be used to recycle process heat. Various fluids may pass through these heat exchangers, such as cooling waters 142, steam 148, and fuel 150. In one heat exchanger 140, steam 86 from dewatering system 40 may be used as a heat source then collected in condenser 152 where carbon dioxide 154 may be separated from water 156, which may be returned to fermentation/pretreatment system 10.

Pumps 158 may also be included at various points in the system to facilitate fluid flow.

Figure 4:
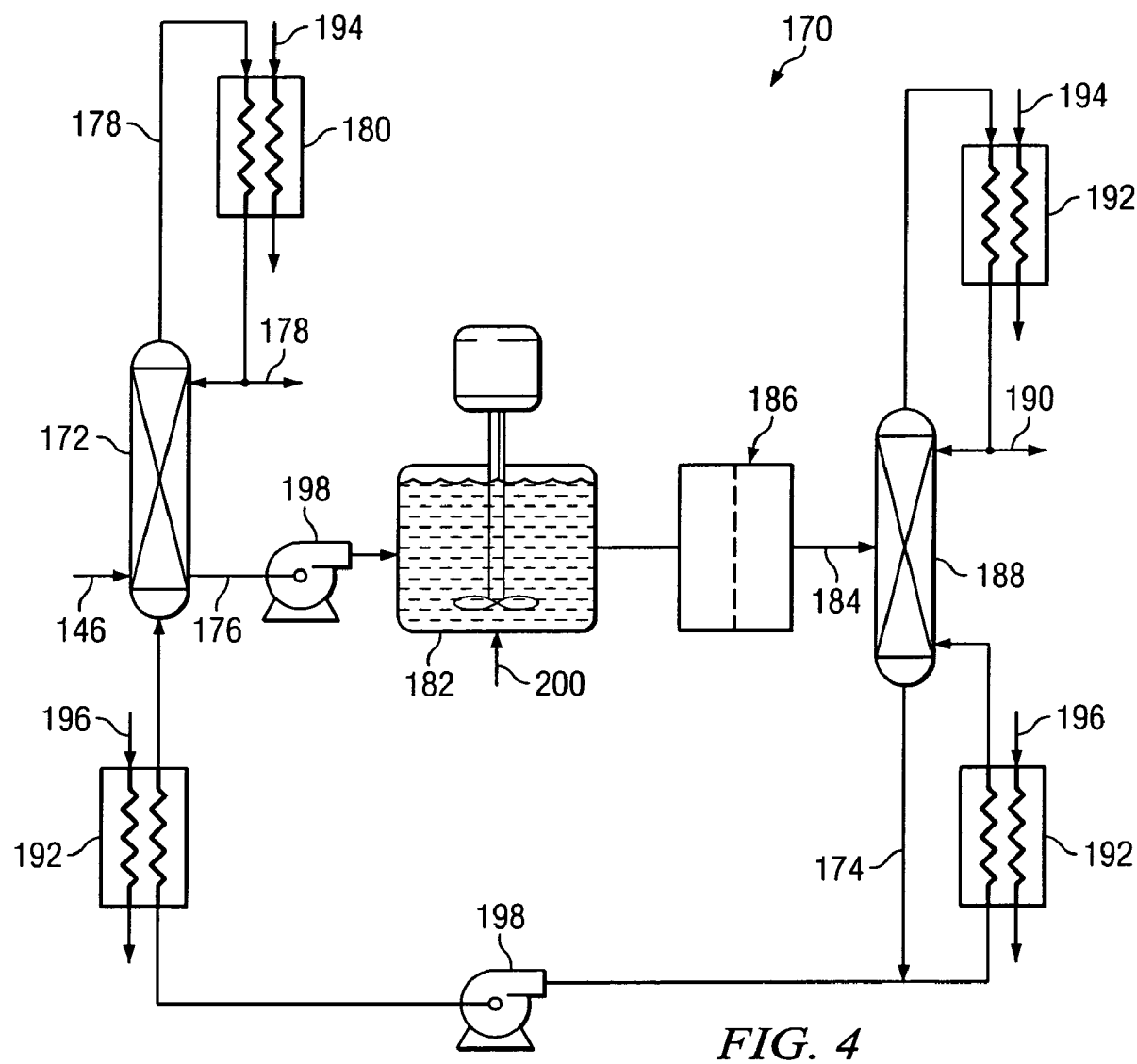
FIG. 4 illustrates a hydrogenation system, according to an embodiment of the present invention.

Referring now to FIG. 4, mixed carboxylic acids 146 from acid springing system 90 may be sent to hydrogenation system 170. Mixed acids 146 may be placed in column 172 and combined with high-molecular-weight alcohol 174 such as heptanol. Carboxylic acids 146 react with alcohol 174 to form ester 176 and water 178. Water 178 may be separated in column 172 and sent to heat exchanger 180 then returned to column 172 or used elsewhere in systems 10, 40, 90 or 170. Ester 176 may be sent to hydrogenation reactor 182 which contains a suitable hydrogenation catalyst, such as a Raney nickel. In reactor 182, hydrogen 200 is added and ester 176 is converted to alcohol. Solids may be separated from alcohol 184 using solids separator 186. Alcohol mixture 184 may be sent column 188 which may recover high-molecular-weight alcohol 174 from the bottom and alcohol product 190 from the top. Alcohol product 190 may be a primary alcohol.

System 170 may contain various heat exchangers 192 that may be used to recycle process heat. Various fluids may pass through these heat exchangers, such as cooling waters 194 and steam 196. Pumps 198 may also be included at various points in the system to facilitate fluid flow.

Alternative systems to recover carboxylic acids without production of alcohol are known in the art any may be used in place of the hydrogenation system of FIG. 4.

Referring now to FIG. 5, system 300 may include as subsystems 302 pretreatment/fermentation system 10, dewatering system 40, acid spring system 90 and optionally also hydrogenation system 170. System 300 may reuse process heat, water, lime, carbon dioxide and other materials among different subsystems 302.

In an alternative embodiment not explicitly shown, ammonia may be used in place of low-molecular-weight tertiary amine 96 in acid spring system 90. Further, if the ammonia is supplied earlier, the a reaction between calcium carboxylate, carbon dioxide and ammonia may occur prior to entry into dewatering system 40. In this embodiment, an aqueous solution of ammonia carboxylate may be evaporated in dewatering system 40 rather than calcium carboxylate. This may help prevent scaling in heat exchangers or system 40 because ammonium salts have a lesser tendency to scale than calcium salts. Ammonia is also cheap and lost ammonia may be diverted to pretreatment/fermentation system 10 where it may serve as a nitrogen source. However, ammonia may react with carboxylic acids to form amides, which may not be a desired byproduct.

Embodiments of the invention may include all processes involved in the operation of the above-described systems. Referring now to FIG. 6, the invention may include an integrated method for producing carboxylic acids and alcohols. The method may include treating pile of biomass 12 with lime or quick lime, water 34, an inoculum and air in step 400 to produce fermentation broth 36. In step 410, fermentation broth 36 may be acidified with high-molecular-weight carboxylic acid 46 then, in step 420, stripped in stripping column 44. In step 430, the product may be concentrated in evaporator 58 to produce concentrated product 68. Concentrated product 68 may be mixed with carbon dioxide 94 and low-molecular-weight tertiary amine 96 in step 440 to form a low-molecular weight tertiary amine carboxylate. This carboxylate may be exchanged with high-molecular-weight tertiary amine 112 in column 110 in step 450 to produce a high-molecular-weight tertiary amine carboxylate. The high-molecular-weight tertiary amine carboxlate may be heated in column 116 to a temperature high enough to break the acid to amine bonds in step 460. This produces carboxylic acids 146 which may be recovered in step 470. In some embodiments, carboxylic acids 146 may be combined with high-molecular-weight alcohol 174 to form ester 176 in step 480. In step 490, ester 176 may be hydrogenated in chamber 182 to form alcohol product 190. In step 500, high-molecular-weight alcohol 174 and alcohol product 190 may be separated in column 188. Alcohol product 190 may be a primary alcohol.

In an alternative embodiment, ammonia may be used in place of low-molecular-weight tertiary amine 96. Ammonia may be added immediately after step 400.

Various methods, systems and apparati useful in the present invention may also be described in U.S. Pat. No. 6,043,392, issued Mar. 28, 2000, U.S. Pat. No. 5,986,133, issued Nov. 16, 1999, U.S. Pat. No. 6,478,965, issued Nov. 12, 2002, U.S. Pat. No. 6,395,926, issued May 28, 2002, U.S. Pat. No. 5,962,307, issued Oct. 5, 1999, and WO 04/041995, published May 21, 2004, and their US and foreign counterpart applications and patents. All of the above patents and applications are incorporated by reference herein.

The invention claimed is:

1. A method of obtaining a fermentation product comprising:
    treating biomass with lime an inoculum to produce a fermentation broth;
    acidifying the fermentation broth to produce acidified fermentation broth;
    stripping the acidified fermentation broth in a stripping column to produce stripped fermentation broth;
    concentrating the stripped fermentation broth in an evaporator to produce a concentrate;
    mixing the concentrate with a first tertiary amine and carbon dioxide to produce a mixture comprising a carboxylate of said first tertiary amine and calcium carbonate;
    removing calcium carbonate from said mixture;
    exchanging the mixture with a second tertiary amine to produce an intermediate comprising a carboxylate of said second tertiary amine, wherein said second tertiary amine has a higher molecular weight than said first tertiary amine; and
    heating the intermediate to a temperature sufficient to break acid/amine bonds to produce at least one free carboxylic acid.

2. The method of claim 1, wherein the biomass comprises lignocellulosic biomass.

3. The method of claim 1 wherein acidifying the fermentation broth comprises utilizing a carboxylic acid to acidify the fermentation broth.

4. The method of claim 3 wherein said carboxylic acid comprises caproic acid, valeric acid, or heptanoic acid.

5. The method of claim 1 wherein said first tertiary amine comprises triethyl amine.

6. The method of claim 1 wherein said second tertiary amine comprises trioctyl amine or triethanol amine.

7. The method of claim 1 further comprising washing or steam stripping the removed calcium carbonate.

8. The method of claim 1 further comprising pretreating the biomass with lime or quick lime, and water prior to treating the biomass with the inoculum.

9. The method of claim 1 further comprising pretreating the biomass with lime or quick lime, water, and air prior to treating the biomass with the inoculum.

10. The method of claim 1 further comprising recycling the removed calcium carbonate to pretreat the biomass.

11. The method of claim 1 further comprising converting the removed calcium carbonate to quick lime.

12. The method of claim 11 further comprising recycling said quick lime to pretreat the biomass.

13. The method of claim 1 further comprising adjusting the pH of the stripped fermentation broth with lime after stripping the acidified fermentation broth.

14. The method of claim 1 further comprising recovering said free carboxylic acid.

* * * * *